US011173326B2

(12) United States Patent
Yang et al.

(10) Patent No.: US 11,173,326 B2
(45) Date of Patent: Nov. 16, 2021

(54) LEAF POSITIONING DEVICE FOR MULTI-LEAF COLLIMATOR

(71) Applicant: OUR UNITED CORPORATION, Shaanxi (CN)

(72) Inventors: Bin Yang, Shaanxi (CN); Mengmeng Zhang, Shaanxi (CN)

(73) Assignee: OUR UNITED CORPORATION, Shaanxi (CN)

( * ) Notice: Subject to any disclaimer, the term of this patent is extended or adjusted under 35 U.S.C. 154(b) by 215 days.

(21) Appl. No.: 16/472,709

(22) PCT Filed: Aug. 7, 2017

(86) PCT No.: PCT/CN2017/096216
§ 371 (c)(1),
(2) Date: Jun. 21, 2019

(87) PCT Pub. No.: WO2018/113310
PCT Pub. Date: Jun. 28, 2018

(65) Prior Publication Data
US 2021/0146155 A1    May 20, 2021

(30) Foreign Application Priority Data

Dec. 21, 2016 (CN) .......................... 201621405022.7

(51) Int. Cl.
*A61N 5/10* (2006.01)
(52) U.S. Cl.
CPC ......... *A61N 5/1045* (2013.01); *A61N 5/1049* (2013.01); *A61N 2005/105* (2013.01)
(58) Field of Classification Search
None
See application file for complete search history.

(56) References Cited

U.S. PATENT DOCUMENTS

| 10,518,110 | B1* | 12/2019 | Jimenez-Carvajal ....................... G21K 1/046 |
| 2008/0298553 | A1* | 12/2008 | Takahashi ............ A61N 5/1042 378/152 |

(Continued)

FOREIGN PATENT DOCUMENTS

| CN | 2523447 Y | 12/2002 |
| CN | 102755696 A | 10/2012 |

(Continued)

OTHER PUBLICATIONS

International Search Report and Written Opinion for PCT/CN2017/096216, dated Nov. 3, 2017.

*Primary Examiner* — Hoon K Song
(74) *Attorney, Agent, or Firm* — Marshall, Gerstein & Borun LLP (57) ABSTRACT

Disclosed a leaf positioning device (100) for a multi-leaf collimator, comprising: a plurality of positioning signal transmitters which are in the leaf guide rail box, wherein the plurality of positioning signal transmitters are arranged opposite to a first end surface of leaves of the multi-leaf collimator; a plurality of positioning signal receivers which are in the leaf guide rail box and corresponding to the plurality of positioning signal transmitters, wherein the plurality of positioning signal receivers are arranged opposite to a second end surface of the leaves of the multi-leaf collimator; wherein, the plurality of positioning signal transmitters are configured to transmit positioning signals to the plurality of positioning signal receivers, and the plurality of positioning signal receivers are configured to generate output signals according to the positioning signals; a positioning device which is connected to each of the plurality of positioning signal receivers, wherein the positioning device is configured to receive the output signals sent out by each (Continued)

of the plurality of positioning signal receivers, and positions the leaves of the multi-leaf collimator according to the output signals.

11 Claims, 4 Drawing Sheets

(56) References Cited

U.S. PATENT DOCUMENTS

| | | | | |
|---|---|---|---|---|
| 2009/0080619 A1* | 3/2009 | Hasegawa | ............... | G21K 1/046 378/151 |
| 2013/0003080 A1* | 1/2013 | Humphrey | ............... | G01S 17/42 356/614 |

FOREIGN PATENT DOCUMENTS

| | | |
|---|---|---|
| CN | 104147712 A | 11/2014 |
| CN | 104667427 A | 6/2015 |

* cited by examiner

LEAF POSITIONING DEVICE FOR MULTI-LEAF COLLIMATOR

CROSS-REFERENCE TO RELATED APPLICATION

This application is a national phase entry under 35 USC 371 of International Patent Application No. PCT/CN2017/096216 filed on Aug. 7, 2017, which claims priority to Chinese Patent Application No. 201621405022.7 filed on Dec. 21, 2016, titled "LEAF POSITIONING DEVICE FOR MULTI-LEAF COLLIMATOR", which are incorporated herein by reference in their entirety.

TECHNICAL FIELD

The present disclosure relates to the field of radiotherapy equipment, more particularly, to a leaf positioning device for a multi-leaf collimator.

BACKGROUND

The multi-leaf collimator is an essential component which is indispensable for precision radiotherapy in modern radiotherapy equipment. The positioning of leaves is one of the key technologies. In the prior art, the positioning of leaves is usually completed by using a motor encoder mounted on an end of a motor shaft to measure the number of rotations of the motor, then a motion displacement of each leaf can be obtained according to the number of rotations of the motor, so as to obtain the present position of each leaf according to the motion displacement of each leaf and an original position of each leaf. The motor is connected with the leaves through transmission mechanism such as a coupling and a screw rod. The motor encoder is located at another end of the motor opposite to the leaves. When the movement of the leaves is driven by the screw rod which is driven by the motor through the coupling, the reading of the motor encoder reflects the number of rotations of the motor. The positions of the leaves can be estimated by the mechanical structure and the corresponding calculation formula.

However, in this method, the rotation of the motor drives the leaves through a series of transmission mechanisms, and installation tolerance inevitably exists among the transmission mechanisms. Therefore, there is an error between the actual moving positions of the leaves and the positions of the leaves obtained by the motor encoder based on the number of rotations of the motor, which will result in low measurement accuracy of the motor encoder. And the method cannot directly measure the positions of the leaves, the actual positions of the leaves cannot be reflected at all once the screw rod slips out. The positional accuracy of the leaves seriously affects the accuracy of the radiation field formed by the multi-leaf collimator, and which is an important factor affecting the effect of high-precision radiotherapy methods such as intensity modulated radiation therapy.

SUMMARY

The technical problem mainly solved by the present disclosure is to provide a leaf positioning device for a multi-leaf collimator, which can position each leaf of the multi-leaf collimator by directly reading the position where each leaf is currently located, and then the movement of the leaves is controlled precisely cooperating with a screw rod.

In order to solve the above technical problem, the technical solution adopted by the present disclosure is to provide a leaf positioning device for a multi-leaf collimator. The leaf positioning device comprises: a plurality of positioning signal transmitters which are in the leaf guide rail box, wherein the plurality of positioning signal transmitters are arranged opposite to a first end surface of leaves of the multi-leaf collimator; a plurality of positioning signal receivers which are in the leaf guide rail box and corresponding to the plurality of positioning signal transmitters, wherein the plurality of positioning signal receivers are arranged opposite to a second end surface of the leaves of the multi-leaf collimator; wherein, the plurality of positioning signal transmitters are configured to transmit positioning signals to the plurality of positioning signal receivers, and the plurality of positioning signal receivers are configured to generate output signals according to the positioning signals; a positioning device which is connected to each of the plurality of positioning signal receivers, wherein the positioning device is configured to receive the output signals sent out by each of the plurality of positioning signal receivers, and positions the leaves of the multi-leaf collimator according to the output signals.

Herein, the plurality of positioning signal transmitters and the plurality of positioning signal receivers are all provided in a matrix.

Herein, the plurality of positioning signal transmitters are provided on a transmitting plate, and the plurality of positioning signal receivers are provided on a receiving plate; wherein the transmitting plate and the receiving plate are oppositely provided on the leaf guide rail box of the multi-leaf collimator.

Herein, the plurality of positioning signal transmitters are provided on the transmitting plate in a patch-type, plug-in type or welding and the plurality of positioning signal receivers are provided on the receiving plate in a patch-type, plug-in type or welding.

Herein, a positioning signal is an electromagnetic wave signal.

Herein, in a matrix of electromagnetic wave signal transmitters formed by the plurality of positioning signal transmitters, adjacent electromagnetic wave signal transmitters transmit electromagnetic wave signals at different transmitting frequencies in the matrix of the electromagnetic wave signal transmitters.

Herein, the transmitting plate and the receiving plate are fixed on a leaf guide rail box cover plate or integrally formed with the leaf guide rail box.

Herein, both the transmitting plate and the receiving plate are connected to the leaf fixing frame, and a radiation protection plate is provided on a side of the transmitting plate facing away from the plurality of positioning signal transmitters and a radiation protection plate is provided on a side of the receiving plate facing away from the plurality of positioning signal receivers.

Herein, the positioning device includes a receiving unit, a signal-shaping circuit and an encoder connected sequentially. The signal-shaping circuit is connected to the receiving unit and the encoder, and the encoder is connected to the positioning signal receivers to encode the positioning signal received by the positioning signal receivers to generate data.

Herein, the positioning device further includes a level conversion unit, the level conversion unit is connected to the signal-shaping circuit and the encoder.

Herein, the positioning device further includes an output unit connected to the encoder, an output end of the output unit is connected to a display device or directly output to a collimator control unit.

The leaf positioning device for a multi-leaf collimator of the present disclosure can be distinguished from the prior art, the device comprising: a plurality of positioning signal transmitters which are in the leaf guide rail box, wherein the plurality of positioning signal transmitters are arranged opposite to a first end surface of leaves of the multi-leaf collimator; a plurality of positioning signal receivers which are in the leaf guide rail box and corresponding to the plurality of positioning signal transmitters, wherein the plurality of positioning signal receivers are arranged opposite to a second end surface of the leaves of the multi-leaf collimator; wherein, the plurality of positioning signal transmitters are configured to transmit positioning signals to the plurality of positioning signal receivers, and the plurality of positioning signal receivers are configured to generate output signals according to the positioning signals; a positioning device which is connected to each of the plurality of positioning signal receivers, wherein the positioning device is configured to receive the output signals sent out by each of the plurality of positioning signal receivers, and positions the leaves of the multi-leaf collimator according to the output signals. The present disclosure can roughly position the position of each leaf of the multi-leaf collimator, directly reading the position where each leaf is currently located, and precisely controlling the movement of the leaves cooperating with a screw rod.

DETAILED DESCRIPTION

The technical solution of the present disclosure is further described in more detail below in combination with the specific embodiments. Obviously, the described embodiments are only part of the embodiments but not all of embodiments of the present disclosure. Based on the embodiments of the present disclosure, all other embodiments obtained by the person skilled in the art without creative efforts shall be included in the protection scope of the present disclosure.

The multi-leaf collimator is an essential component which is indispensable for precision radiotherapy in modern radiotherapy equipment. The positioning of leaves is one of the key technologies. In the prior art, there are mainly the following three methods for detecting positions of the leaves when the leaves is positioned.

In a first method, the positioning of the leaves is usually completed by using a motor encoder mounted on an end of a motor shaft to measure the number of rotations of the motor, then a motion displacement of each leaf can be obtained according to the number of rotations of the motor, so as to obtain the position of each leaf according to the motion displacement and an original position of each leaf. The motor is connected with the leaves through transmission mechanism such as a coupling and a screw rod. The motor encoder is located at another end of the motor opposite to the leaves. When the movement of the leaves is driven by the screw rod and the screw rod is driven by the motor through the coupling, the reading of the motor encoder reflects the number of rotations of the motor. The positions of the leaves can be estimated by the mechanical structure and the corresponding calculation formula. However, in this method, the rotation of the motor drives the leaves through a series of transmission mechanisms, and installation tolerance inevitably exists among the transmission structures. Therefore, there is an error between the actual positions of the leaves and the positions of the leaves obtained by the motor encoder based on the number of rotations of the motor, which will result in low measurement accuracy of the motor encoder. In extreme cases, when the mechanical system fails, such as a sliding wire between the screw rod and a screw nut, the reading of the motor encoder does not reflect the actual positions of the leaves.

A second detecting method is to use a potentiometer mounted on an end of the motor shaft to perform detection. The potentiometer can convert a mechanical displacement into a resistance or voltage output which has a definite relationship with the mechanical displacement. When the motor drives the leaves to move, the motor also drives a movable end of the potentiometer to move, and the resistance of the potentiometer changes. The variation of the resistance reflects the magnitude of the displacement, and the increase or decrease of the resistance indicates a direction of the displacement. A high-precision linear potentiometer having good linearity and precision is adopted. The disadvantages include too much wiring, high failure rate, difficult maintenance, needing high-precision linear potentiometer, and a brush on the moving end of the potentiometer is easy to be worn out and its service life is short.

A third detecting method employs an optical imaging device. The optical imaging device simulates the radiation field of radioactive ray using visible light, and the light field of visible light is the same as the radiation field of the radioactive ray. Therefore, the positions of the leaves are adjusted according to the light field formed by the visible light passing through the multi-leaf collimator. However, the visible light in the optical imaging device is easily interfered by ambient light, and when the ambient light is relatively strong, the monitoring accuracy of the optical imaging device is relatively low. Therefore, there is a problem of poor anti-jamming performance in monitoring positions of the leaves by using optical imaging device.

The positional accuracy of the leaves seriously affects the accuracy of the radiation field formed by the multi-leaf collimator, and which is an important factor affecting the effect of high-precision radiotherapy methods such as intensity modulated radiation therapy. In view of the deficiencies of the prior art, the present disclosure provides a leaf positioning device for a multi-leaf collimator.

Figure 1:
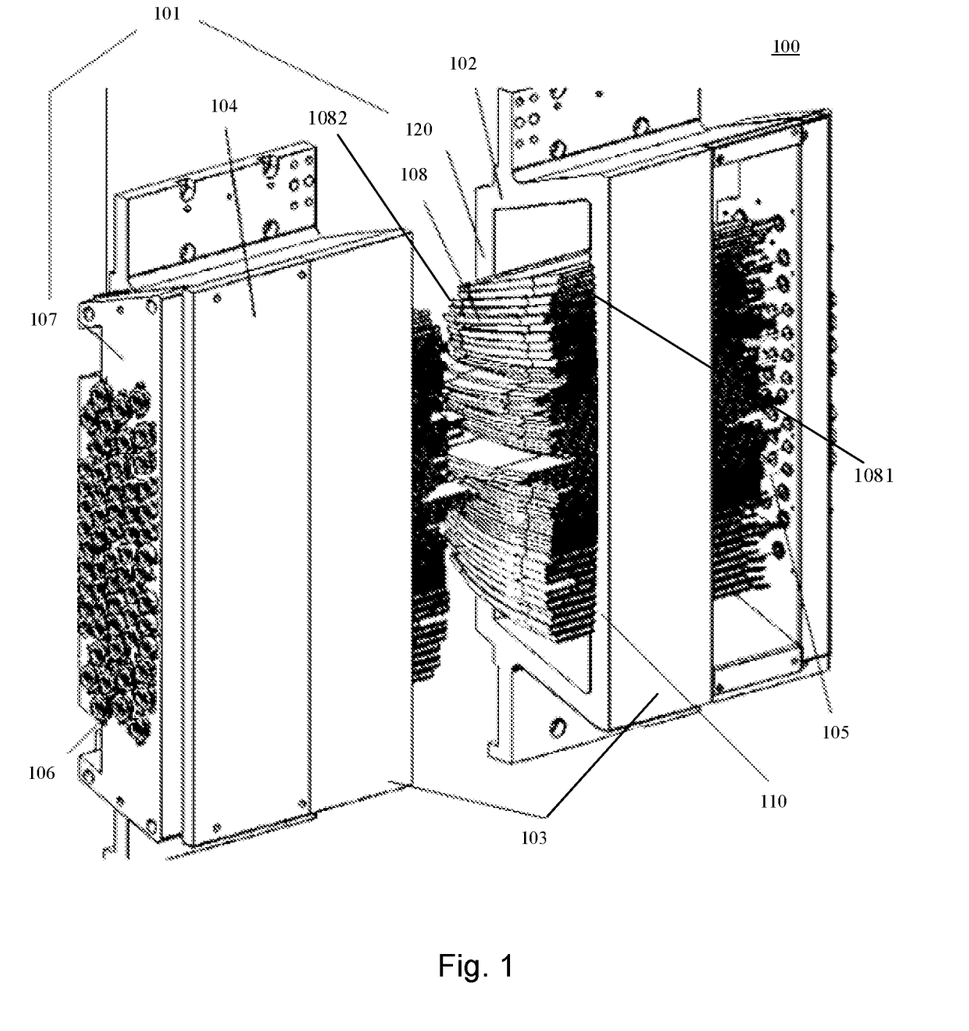
FIG. 1 is a structural diagram of an embodiment of a leaf positioning device for a multi-leaf collimator observed from outside according to the present disclosure.
Figure 2:
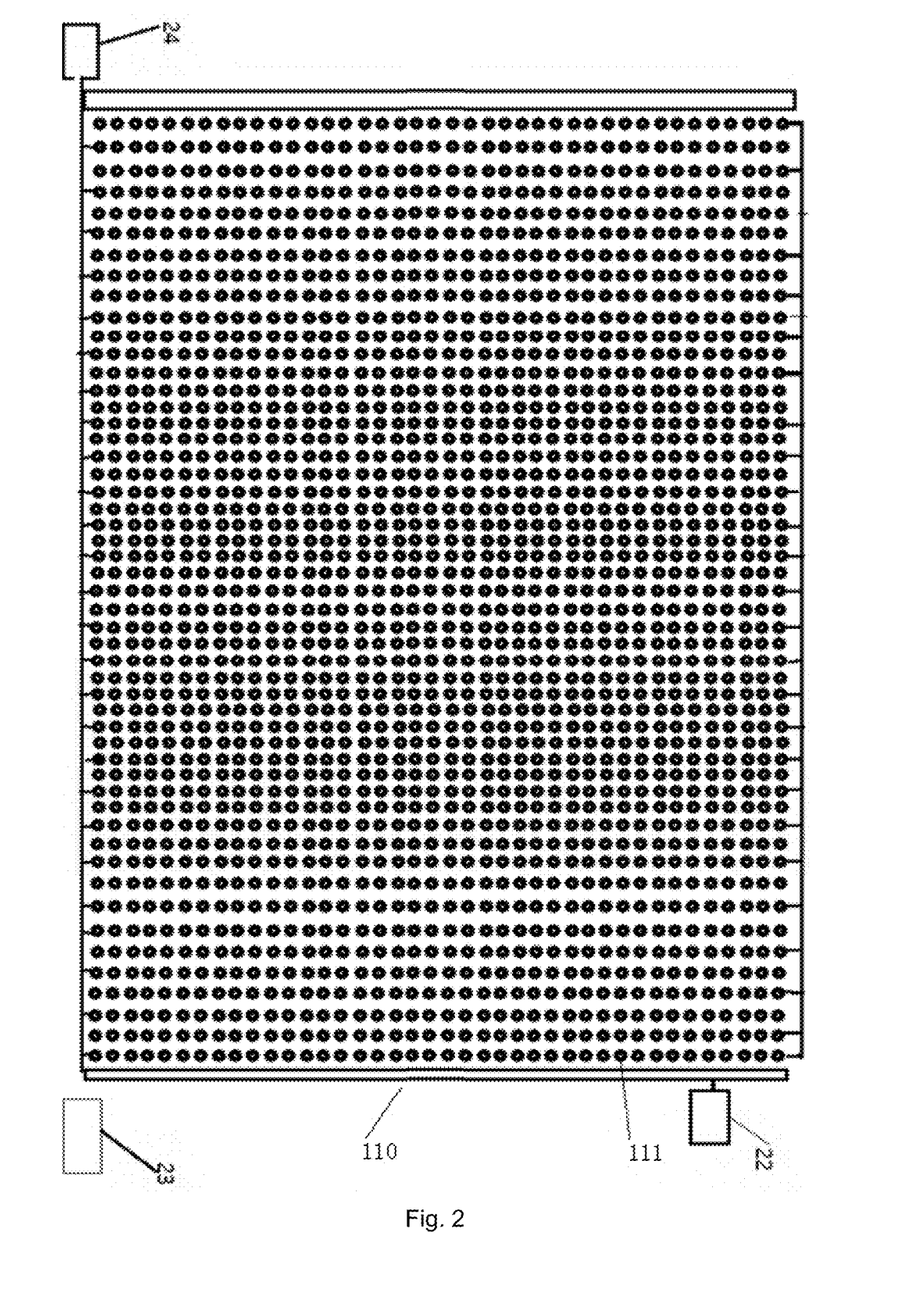
FIG. 2 is a structural diagram of a transmitting plate of a leaf positioning device for a multi-leaf collimator according to the present disclosure.
Figure 3:
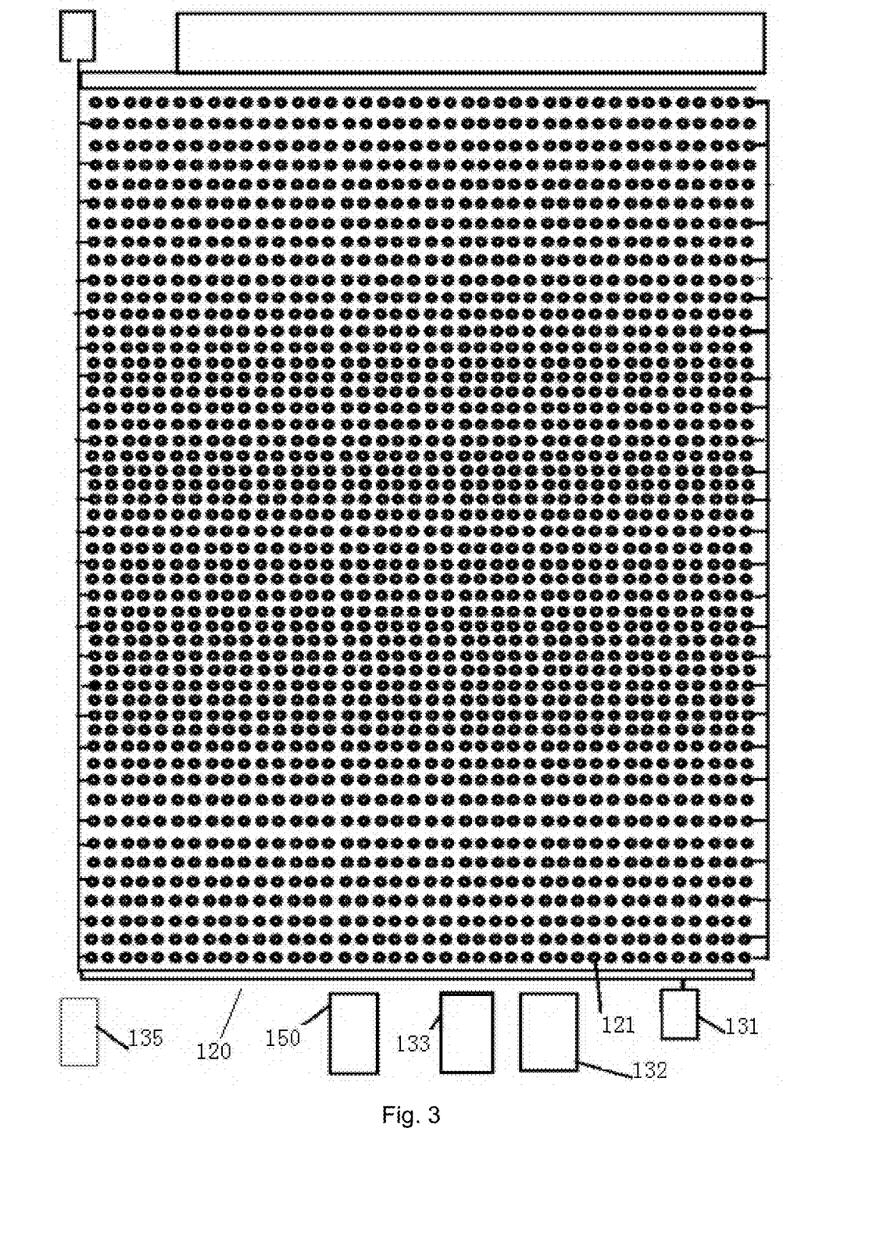
FIG. 3 is a structural diagram of a receiving plate of a leaf positioning device for a multi-leaf collimator according to the present disclosure.

Referring to FIG. 1, FIG. 1 is a structural diagram of an embodiment of a leaf positioning device for a multi-leaf collimator provided by the present disclosure. The leaf positioning device 100 is disposed on a leaf guide rail box 101 of a multi-leaf collimator of a radiotherapy apparatus, and includes a transmitting plate 110, a receiving plate 120, and a positioning device 130. The structure of the transmitting plate 110 and the receiving plate 120 is blocked by an upper surface 103 of the leaf guide rail box and the leaves 108 in FIG. 1. The structure of the transmitting plate 110 is as shown in FIG. 2. The structure of the receiving plate 120 is as shown in FIG. 3.

The multi-leaf collimator of the radiotherapy equipment includes a leaf shielding cover plate 104, an upper surface 103 of the leaf guide rail box, and the leaf guide rail box 101 composed of a motor mounting frame 107 and a leaf fixing frame 102, and the leaves 108 moving in the leaf guide rail box 101. A motor mounted on each motor mounting base 106 in the motor mounting frame 107 controls each leaf 108 to move by driving a screw rod 105 that connects each leaf. The leaf fixing frame 102 is provided in parallel with the leaves for fixing the leaves, so as to prevent the leaves from scattering and providing a sliding guide for the leaves.

The transmitting plate 110 and the receiving plate 120 are provided opposite to each other on the upper and lower sides of the leaves 108 in the leaf guide rail box 101, forming a surface of a cubic structure of the leaf guide box 101 cooperated with the leaf fixing frame 102 and the motor mounting frame 107. The transmitting plate 110 is directly fixed under a leaf guide rail box cover plate 104, and the receiving plate 120 is directly fixed under the leaves of the leaf guide rail box 101 or the transmitting plate 110 and the receiving plate 120 are integrally formed with the leaf guide rail box 101. The mounting positions of the transmitting plate 110 and the receiving plate 120 can be interchanged. A plurality of positioning signal transmitters 111 are provided on the transmitting plate 110, and correspondingly, a plurality of positioning signal receivers 121 are provided on the receiving plate 120 with the same number as the plurality of positioning signal transmitters 111. The positioning signal transmitted by the plurality of positioning signal transmitters 111 is received by the corresponding the plurality of positioning signal receivers 121 on the receiving plate 120.

In the present embodiment, each leaf 108 of the multi-leaf collimator has a terminal end surface, a front end surface, and upper and lower end surfaces. Among them, the front end surface is directed to a traveling direction of the leaves 108, the terminal end surface is connected to the screw rod 105, and the upper end surface and the lower end surface are facing the transmitting plate 110 and the receiving plate 120, respectively (that is, the upper end surfaces of the leaves 108 are arranged opposite to the plurality of positioning signal transmitters 111, and the lower end surfaces of the leaves 108 are arranged opposite to the plurality of positioning signal receivers 121). However, in some embodiments, the upper end surfaces of the leaves 108 are arranged opposite to the plurality of positioning signal receivers 121, and the lower end surfaces of the leaves 108 are arranged opposite to the plurality of positioning signal transmitters 111. An end surface of each leaf 108 that is opposite to the plurality of positioning signal transmitters 111 is called as a first end surface 1081, and an end surface of each leaf 108 that is opposite to the plurality of positioning signal receivers is called as a second end surface 1082. The positioning signal transmitters 111 and the positioning signal receivers 121 are respectively facing the upper end surface and the lower end surface of the leaves 108, for example, facing the center positions of the leaves near the last segments of the upper end surface and the lower end surface. The plurality of positioning signal transmitters 111 and the plurality of positioning signal receivers 121 are all provided on the transmitting plate 110 and the receiving plate 120 in a patch-type, plug-in type or welding. The plurality of positioning signal transmitters 111 and the plurality of positioning signal receivers 121 are arranged in a matrix on the surfaces of the transmitting plate 110 and the receiving plate 120, as shown in FIG. 2 and FIG. 3.

In FIG. 2, the transmitting plate 110 is also provided with a modulation circuit 22 and a positioning signal transmission control circuit 23. The plurality of positioning signal transmitters transmit positioning signals with different frequency characteristics by the modulation of the modulation circuit 22, to avoid mutual interference of adjacent beams. For example, in the present embodiment, the positioning signals transmitted by each column of the positioning signal transmitters 111 in the matrix are set as a arithmetic progression by the modulation circuit 23, or the positioning signals can also be set as other forms such as a geometric progression; the plurality of positioning signal transmitters 111 are controlled to transmit the positioning signals by the positioning signal transmission control circuit 23. The positioning signal is a spatial wave signal that propagates in a straight line, such as a laser, an infrared ray, ultraviolet or visible light. A power supply port 24 is also included by the transmitting plate 110 to provide power for the plurality of positioning signal transmitters 111. Transmitting paths of the positioning signals emitted by the plurality of positioning signal transmitters 111 are parallel with a plane formed by the movement of the leaves 108 of the multi-leaf collimator. In the present embodiment, 60×12 positioning signal transmitters 111 can be provided on the transmitting plate 110, and the same number of the positioning signal receivers 121 corresponding to the positions of the positioning signal transmitters 111 are provided on the receiving plate 120. Each positioning signal transmitter 121 is such as a laser emitting diode, and each positioning signal receiver 121 receives a corresponding laser beam emitted by the laser emitting diode.

A radiation protection plate (for example, a leaf shielding cover plate 104) is provided on a side of the transmitting plate 110 facing away from the plurality of positioning signal transmitters 111, and a radiation protection plate (for example, a leaf shielding cover plate 104) is provided on a side of the receiving plate 120 facing away from the plurality of positioning signal receivers 121.

Figure 4:
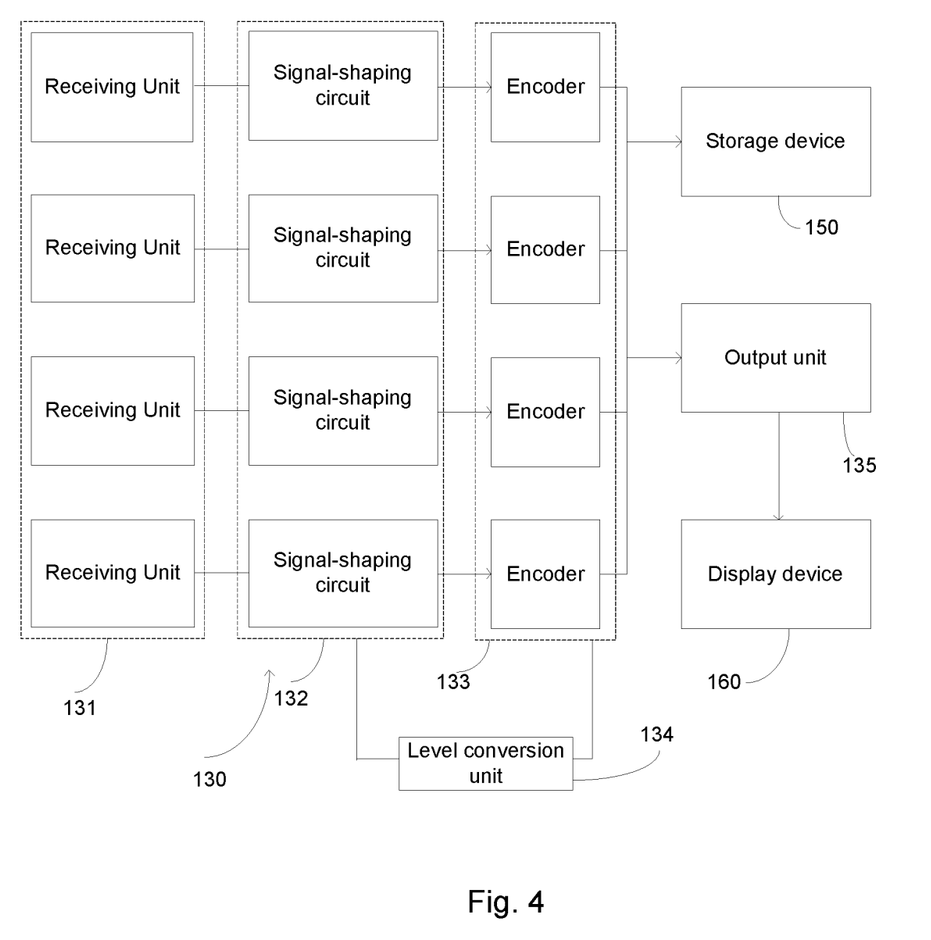
FIG. 4 is a structural diagram of a positioning module of a leaf positioning device for a multi-leaf collimator according to the present disclosure.

The positioning device 130 includes a plurality of receiving units 131, a plurality of signal-shaping circuits 132, and a plurality of encoders 133. Each receiving unit 131, each signal-shaping circuit 132 and each encoder 133 are connected sequentially in a one-to-one correspondent way, wherein each signal shaping circuit 132 is connected to a receiving unit 131 and an encoder 133. The plurality of encoders 133 are further connected to a storage device 150. The positioning device 130 further includes a level conversion unit 134 and an output unit 135 connected to the plurality of encoders 133. The level conversion unit 134 is connected to the plurality of signal-shaping circuits 132 and the plurality of encoders 133. The output end of the output unit 135 is connected to a display device 160. In some embodiments, the output end of the output unit 135 is coupled to collimator control unit.

Each receiving unit 131 is composed of a receiving diode or a photosensitive element and their corresponding auxiliary circuit, and each receiving unit 131 is correspondingly connected to each positioning signal receiver 121 for converting the positioning signal received by the positioning signal receivers 121 into an identifiable signal; each signal-shaping circuit 132 is used for signal shaping of the identifiable signal converted by the receiving unit; each encoder 133 encodes the signal has been shaped and then outputs the encoding results, and the encoding results are stored in the storage device 150 connected to the plurality of encoders 133. For example, each positioning signal transmitter 111 is a laser diode, and a laser signal transmitted by each positioning signal transmitter 111 is received by the corresponding positioning signal receiver 121, and then the laser signal is converted into an electrical signal with a certain waveform by the receiving diode and its auxiliary circuit. Each signal-shaping circuit 132 converts the received electrical signal into a digital pulse signal, each encoder 133 encodes the output digital pulse signal, and outputs figures indicating the state of the switch, and the figures are stored in the storage device 150 for output and display at any time. A circuit structure of the positioning device 130 is shown in FIG. 4.

The leaves of the multi-leaf collimator include two sets of leaves, so that the transmitting plate 110 and the receiving plate 120 are respectively provided on both sides of each set of the two sets of leaves. An initial position of each leaf is close to the corresponding motor mounting base 106, at this time the two sets of leaves are separated. During the treatment of the radiotherapy equipment, the motor drives the corresponding screw rod 105 to control the movement of each leaf 108. When each leaf 108 is in the initial position, they are between the transmitting plate 110 and the receiving plate 120, and the upper end surface and the lower end surface of each leaf 108 are respectively facing one column of the matrix of the plurality of positioning signal transmitters 111 and one column of the matrix of the plurality of positioning signal receivers 121. At this time, the positioning signals emitted by the plurality of positioning signal transmitters 111 cannot be received by the corresponding positioning signal receivers 121. The initial position of each leaf 108 can be the position of the motor mounting base 106 provided adjacent to both sides of the leaf guide rail box 101, or a middle position of the leaf guide rail box can be used as the initial position when both sets of the leaves are in the middle position of the leaf guide rail box 101. When each leaf is in the initial position, each column of the positioning signal transmitters 111 which are set in a matrix and each column of the positioning signal receivers 121 opposite to them which are set in a matrix are facing the upper and lower end surfaces of the leaves 108. During the movement of the leaves from the initial position, the two sets of leaves may move in opposite directions or in reverse directions. When one leaf 108 moves from the initial position, the positioning signal transmitters 111 and the positioning signal receivers 121 corresponding to this leaf 108 face a center position of the upper end surface and the lower end surface at the last segment of this leaf, when this leaf 108 moves partially out of the coverage of the transmitting plate 110 and the receiving plate 120, the positioning signals transmitted by partial positioning signal transmitters 111 are received by the corresponding positioning signal receivers 121 due to the movement of this leaf 108, and the corresponding positioning signal receivers 121 transmit the signals to the positioning device 130. A circuit structural diagram of the receiving plate 120 is shown in FIG. 3. The positioning device 130 calculates the relative position of each leaf according to the mounting position and state of the positioning signal receivers 121. The number of the plurality of positioning signal transmitters 111 and the plurality of positioning signal receivers 121 is increased or decreased depending on the number of actual leaves. The plurality of receiving unit 131, the plurality of signal-shaping circuits 132, the plurality of encoders 133, and the storage device 150 are all provided in an integrated circuit of the receiving plate 120. The integrated circuit is, for example, implemented by a field programmable gate array (FPGA). Optionally, the power supply control signal of the plurality of positioning signal transmitters 111 is given by the FPGA gating circuit, and the occasion and time of the emission can be controlled to reduce the system power consumption.

In the present embodiment, when the leaves are in the initial position, all of the positioning signal receivers 121 are not provided with the positioning signals, and the positioning signal receivers 121 are in off state without light; When the leaves move, the positioning signal receivers 121 disposed on a portion of the receiving plate that is no longer covered by the leaves 108 are sequentially turned on one by one by receiving the positioning signals. According to the positions of the positioning signal receivers 121 switched on, the positions of the leaves can be estimated and it can be used to calibrate the coding accuracy of multi-leaf collimator.

The leaf positioning device for a multi-leaf collimator of the present disclosure can be distinguished from the prior art. The device comprises: a plurality of positioning signal transmitters which are in the leaf guide rail box, wherein the plurality of positioning signal transmitters are arranged opposite to a first end surface of leaves of the multi-leaf collimator; a plurality of positioning signal receivers which are in the leaf guide rail box and corresponding to the plurality of positioning signal transmitters, wherein the plurality of positioning signal receivers are arranged opposite to a second end surface of the leaves of the multi-leaf collimator; wherein, the plurality of positioning signal transmitters are configured to transmit positioning signals to the plurality of positioning signal receivers, and the plurality of positioning signal receivers are configured to generate output signals according to the positioning signals; a positioning device which is connected to each of the plurality of positioning signal receivers, wherein the positioning device is configured to receive the output signals sent out by each of the plurality of positioning signal receivers, and positions the leaves of the multi-leaf collimator according to the output signals. The present disclosure can roughly determine the position of each leaf of the multi-leaf collimator, directly read the position where each leaf is currently located, and then precisely control the movement of the leaves cooperating with a screw rod.

The above description is only one embodiment of the present disclosure, and thus does not limit the patent scope of the present invention. Any equivalent structure or equivalent process transformation, or directly or indirectly used in other related technical fields by the specification and the drawings content of the present disclosure, are all included in the scope of patent protection of the present invention.

What is claimed is:

1. A leaf positioning device for a multi-leaf collimator, provided on a leaf guide rail box of a multi-leaf collimator of a radiotherapy apparatus, the leaf positioning device comprises:
   a plurality of positioning signal transmitters which are in the leaf guide rail box, wherein the plurality of positioning signal transmitters are arranged opposite to a first end surface of leaves of the multi-leaf collimator;
   a plurality of positioning signal receivers which are in the leaf guide rail box and corresponding to the plurality of positioning signal transmitters, wherein the plurality of positioning signal receivers are arranged opposite to a second end surface of the leaves of the multi-leaf collimator;
   wherein, the plurality of positioning signal transmitters are configured to transmit positioning signals to the plurality of positioning signal receivers, and the plurality of positioning signal receivers are configured to generate output signals according to the positioning signals;

a positioning device which is connected to each of the plurality of positioning signal receivers, wherein the positioning device is configured to receive the output signals sent out by each of the plurality of positioning signal receivers, and positions the leaves of the multi-leaf collimator according to the output signals.

2. The leaf positioning device for a multi-leaf collimator according to claim 1, wherein, the plurality of positioning signal transmitters and the plurality of positioning signal receivers are provided in a matrix.

3. The leaf positioning device for a multi-leaf collimator according to claim 1, wherein, the plurality of positioning signal transmitters are provided on a transmitting plate, and the plurality of positioning signal receivers are provided on a receiving plate;
wherein the transmitting plate and the receiving plate are oppositely provided on the leaf guide rail box of the multi-leaf collimator.

4. The leaf positioning device for a multi-leaf collimator according to claim 3, wherein, the positioning signal transmitters are provided on the transmitting plate in a patch-type, plug-in type or welding, and the plurality of positioning signal receivers are provided on the receiving plate in a patch-type, plug-in type or welding.

5. The leaf positioning device for a multi-leaf collimator according to claim 1, wherein, a positioning signal is an electromagnetic wave signal.

6. The leaf positioning device for a multi-leaf collimator according to claim 5, wherein, in a matrix of electromagnetic wave signal transmitters formed by the plurality of positioning signal transmitters, adjacent electromagnetic wave signal transmitters transmit the electromagnetic wave signals at different transmitting frequencies.

7. The leaf positioning device for a multi-leaf collimator according to claim 3, wherein, the transmitting plate and the receiving plate are fixed on a leaf guide rail box cover plate or integrally formed with the leaf guide rail box.

8. The leaf positioning device for a multi-leaf collimator according to claim 7, wherein, both the transmitting plate and the receiving plate are connected to a leaf fixing frame, and a radiation protection plates is provided on a side of the transmitting plate facing away from the plurality of positioning signal transmitters and a radiation protection plate is provided on a side of the receiving plate facing away from the plurality of positioning signal receivers.

9. The leaf positioning device for a multi-leaf collimator according to claim 1, wherein, the positioning device includes a receiving unit, an encoder and a signal-shaping circuit unit and an encoder connected sequentially, the signal-shaping circuit unit is connected to the receiving unit and the encoder.

10. The leaf positioning device for a multi-leaf collimator according to claim 9, wherein, the positioning device further includes a level conversion unit, and the level conversion unit is connected to the signal-shaping circuit unit and the encoder.

11. The leaf positioning device for a multi-leaf collimator according to claim 9, wherein, the positioning device further includes an output unit connected to the encoder, an output end of the output unit is connected to a display device or directly output to a collimator control unit.

* * * * *